(12) United States Patent
Gao et al.

(10) Patent No.: US 12,394,048 B2
(45) Date of Patent: Aug. 19, 2025

(54) ULTRASOUND IMAGE PROCESSING FOR OVARIAN IDENTIFICATION

(71) Applicant: TONGJI HOSPITAL AFFILIATED TOTONGJI MEDICAL COLLEGE OF HUAZHONG UNIVERSITY OF SCIENCE AND TECHNOLOGY, Wuhan Hubei Province (CN)

(72) Inventors: Qinglei Gao, Wuhan (CN); Ding Ma, Wuhan (CN); Yue Gao, Wuhan (CN); Xiangchun Li, Wuhan (CN); Shaoqing Zeng, Wuhan (CN); Huayi Li, Wuhan (CN)

(73) Assignee: Tongji Hospital affiliated to Tongji Medical College of Huszhong Univeristy of Science & Technology, Beijing (CN)

( * ) Notice: Subject to any disclaimer, the term of this patent is extended or adjusted under 35 U.S.C. 154(b) by 465 days.

(21) Appl. No.: 17/935,196

(22) Filed: Sep. 26, 2022

(65) Prior Publication Data
US 2023/0316504 A1 Oct. 5, 2023

(30) Foreign Application Priority Data
Mar. 31, 2022 (CN) .......................... 202210331375.0

(51) Int. Cl.
*G06T 7/00* (2017.01)
*G06N 3/045* (2023.01)

(52) U.S. Cl.
CPC ........... *G06T 7/0012* (2013.01); *G06N 3/045* (2023.01); *G06T 2207/20081* (2013.01)

(58) Field of Classification Search
CPC ......... G06T 7/0012; G06T 2207/20081; G06T 2207/10132; G06T 2207/20084; G06T 2207/30096; G06N 3/045; G06N 3/0464; G06N 3/09; G06N 3/08; G06V 10/774; G06V 2201/031; G06V 10/82;
(Continued)

(56) References Cited

U.S. PATENT DOCUMENTS

2016/0275678 A1* 9/2016 Onal ....................... G06V 10/50
2019/0030371 A1* 1/2019 Han ...................... A61N 5/1039
(Continued)

*Primary Examiner* — Van D Huynh
(74) *Attorney, Agent, or Firm* — Fleit Intellectual Property Law; Jon Gibbons (57) ABSTRACT

The present disclosure belongs to the technical field of image processing, and discloses an ultrasound image processing method and system for ovarian cancer, a medium, a device, and a terminal. The method includes: obtaining pelvic ultrasound images and relevant clinical data of a patient; performing pelvic ultrasound image and relevant clinical information cleaning and pelvic ultrasound image quality control; and constructing an image classification model. Areas under the curve (AUCs) of performance of a deep convolutional neural network (DCNN) model based on the pelvic ultrasound image of the present disclosure for distinguishing ovarian cancer and non-cancer in an internal validation set and two external validation sets are 0.911, 0.870, and 0.831 respectively, which are superior to an average of diagnosis of ovarian cancer of 35 radiologists in the internal and external validation sets. An AUC of the DCNN for diagnosis of borderline ovarian tumors is 0.821.

12 Claims, 4 Drawing Sheets

(58) Field of Classification Search
CPC ...... G06V 10/764; G16H 15/00; G16H 30/20; G16H 30/40; G16H 50/20; G16H 50/70; A61B 8/5215

See application file for complete search history.

(56) References Cited

U.S. PATENT DOCUMENTS

| | | | |
|---|---|---|---|
| 2020/0140956 A1* | 5/2020 | Kida | C12N 15/113 |
| 2020/0158733 A1* | 5/2020 | Plebanski | G01N 33/57484 |
| 2020/0395117 A1* | 12/2020 | Schnorr | G06N 3/088 |
| 2023/0298353 A1* | 9/2023 | Ruel | G06T 7/20 |
| | | | 382/103 |
| 2024/0290487 A1* | 8/2024 | Mosadegh | G16H 30/40 |

* cited by examiner

ULTRASOUND IMAGE PROCESSING FOR OVARIAN IDENTIFICATION

CROSS REFERENCE TO RELATED APPLICATION

This patent application claims the benefit and priority of Chinese Patent Application No. 202210331375.0, filed on Mar. 31, 2022, the disclosure of which is incorporated by reference herein in its entirety as part of the present application.

TECHNICAL FIELD

The present disclosure belongs to the technical field of image processing, and in particular, to an ultrasound image processing method and system for ovarian cancer, a medium, a device, and a terminal.

BACKGROUND ART

Pelvic ultrasound is the cornerstone of the current clinical diagnosis of ovarian cancer, but its application in the diagnosis of ovarian cancer is limited due to the lack of sensitivity and specificity of traditional ultrasound. Traditional gynecological ultrasonography mainly focuses on macroscopic features such as the boundary, size, and blood flow signals of adnexal masses and has poor sensitivity and specificity. It is especially difficult to determine the nature of borderline ovarian tumors and small adnexal masses, which is difficult to meet clinical needs. Due to the above limitations, the latest analysis results of the UK Collaborative Trial of Ovarian Cancer Screening (UKCTOCS), the largest ever ovarian cancer screening trial (over 200,000 people), has once again demonstrated that screening with the serum tumor marker CA125 alone or combined with transvaginal ultrasound cannot effectively reduce the mortality of patients with ovarian cancer. Therefore, pelvic ultrasound-based ovarian cancer screening is not recommended for the general population.

The 5-year survival rate for patients with early-stage ovarian cancer is as high as 90%, while that of patients with advanced-stage ovarian cancer is less than 40%. Therefore, improving the detection rate of early-stage ovarian cancer will fundamentally improve the prognosis of patients with ovarian cancer. Improving the specificity of current diagnosis of ovarian cancer will protect the fertility of women in their reproductive age and ovarian function in female patients of all ages, and reduce their mental and economic burden.

Through the above analysis, the problems existing in the prior art are summarized as follows:

(1) The application of traditional ultrasound in the diagnosis of ovarian cancer is limited due to the lack of sensitivity and specificity.

(2) Traditional gynecological ultrasonography is difficult to determine the nature of borderline ovarian tumors and small adnexal masses, which is an unmet clinical need.

(3) The results of the ovarian cancer screening trial show that screening with the serum tumor marker CA125 alone or transvaginal ultrasound screening and their combination cannot effectively reduce the mortality of patients with ovarian cancer.

SUMMARY

In view of the problems existing in the prior art, the present disclosure provides an ultrasound image processing method and system for ovarian cancer, a medium, a device, and a terminal.

The present disclosure is implemented as follows: an ultrasound image processing method for ovarian cancer includes the following steps:
- step I, obtaining pelvic ultrasound images and relevant clinical data of a patient;
- step II, performing pelvic ultrasound image and relevant clinical information cleaning and pelvic ultrasound image quality control; and
- step III, constructing and validating an image classification model.

Further, step I specifically may include:
- retrieving ultrasound images, ultrasound times, ultrasound reports, patient operation times, pathological diagnosis reports, ages, and CA125 information of a target population through a picture archiving and communication system (PACS) or an ultrasound workstation, where the ultrasound report may include a size and nature of a mass, and the pathological diagnosis report may include tumor staging and grading.

Further, a process of performing the pelvic ultrasound image cleaning in step II may include:
- randomly selecting images from all of the pooled pelvic ultrasound images for image annotation; and classifying and marking, by a radiologist, the selected images in terms of whether the images are adnexal images, whether there are lesions, whether there are ascites, whether there are blood flow signals, whether the images are two-dimensional or three-dimensional images, and whether the images fail to be determined; and
- based on the clearly marked images, constructing an automatic image classification model for identifying whether the images are adnexal images, whether there are ascites, whether there is blood flow information, and which dimension the images belongs to, so as to classify all of the images, thereby automatically eliminating ultrasound images without lesions and adnexa in batches for subsequent analysis.

Further, a process of performing the pelvic ultrasound image quality control in step II may include:
- based on images marked by a radiologist, constructing a classifier automatically eliminates non-target images, and eliminates all non-adnexal images and ultrasound images of patients with benign and malignant adnexal lesions without adnexal lesion load in training set images in batches, where if a pathological report of the patient shows ovarian cancer, but an image of cancer foci is incapable of being found from an anatomical position on the image, the image may be eliminated.

Further, step III specifically may include:
- training a deep learning algorithm using a deep convolutional neural network (DCNN) classification model, and mapping image input features to corresponding output labels, where the DCNN algorithm may learn a hierarchical representation from input imaging data, and the model may predict the input data; and the image input features may include image pixels, and the output labels may include benign or malignant;
- performing image classification using a ResNet-18 model and a Darknet-19 model, where layers are functional units of neural networks, learn and store abstract features of input images, and have different functions; iteratively training ResNet-50 and Darknet-19 models for classification of patients with benign and malignant adnexal lesions and control images; and measuring an area under the curve (AUC) by weighting performance, combining the two deep learning models, and evaluating the diagnostic performance of the overall DCNN model using internal and external validation sets; and applying flight data enhancement to each image during training, where dynamic enhancement may produce more training images through image processing; and setting a weight decay rate of 0.0005, and generating class activation maps using global average pooling in the ResNet model, where the image processing may include random cropping, rotation, horizontal or vertical flipping, scaling, translation, and adjustment of saturation and exposure.

Further, n represents a total number of images available for the patient, and Pcancer=[P1, P2, ..., Pn] represents a predicted probability of n images classified as cancer, so as to obtain a predicted score of a single patient level.

A score θ assigned to a single examination is defined as a mean of the log-transformed Pcancer:

$$\theta = -[\ln(1-P1) + \ln(1-P2) + \ldots + \ln(1-Pn)]/n.$$

Predicted scores of the ResNet-50 and the Darknet-19 are combined and weighted by performance:

$$\theta_{combined} = w1 \times \theta ResNet\text{-}50 + w2 \times \theta Darknet\text{-}19.$$

$$w1 = AUCResNet\text{-}50/(AUCResNet\text{-}50 + AUCDarknet\text{-}19), \text{ and } w2 = 1.0 - w1.$$

Another objective of the present disclosure is to provide an ultrasound image processing system for ovarian cancer for implementing the ultrasound image processing method for ovarian cancer, including:

a data acquisition module configured to obtain pelvic ultrasound images and relevant clinical data of a patient;

an image cleaning module configured to perform pelvic ultrasound image and relevant clinical information cleaning;

an image quality control module configured to perform pelvic ultrasound image quality control; and an image classification module configured to construct an image classification model to implement image classification.

Another objective of the present disclosure is to provide a computer device. The computer device includes a memory and a processor, the memory stores a computer program, and when the computer program is executed by the processor, the processor implements the following steps:

obtaining pelvic ultrasound images and relevant clinical data of a patient; performing pelvic ultrasound image cleaning and pelvic ultrasound image quality control; and constructing an image classification model to implement image classification.

Another objective of the present disclosure is to provide a computer-readable storage medium. The computer-readable storage medium stores a computer program. When the computer program is executed by the processor, the processor implements the following steps:

obtaining pelvic ultrasound images and relevant clinical data of a patient; performing pelvic ultrasound image cleaning and quality control; and constructing an image classification model to implement image classification.

Another objective of the present disclosure is to provide an information data processing terminal configured to implement the ultrasound image processing system for ovarian cancer.

In combination with the above technical solutions and the technical problems to be solved, the advantages and positive effects of the technical solutions to be protected by the present disclosure are analyzed from the following aspects:

First, in view of the technical problems existing in the above prior art and the difficulty of solving the problems, in close combination with the technical solutions to be protected by the present disclosure and the results and data in the research and development process, a detailed and profound analysis is made on how the technical solutions of the present disclosure solve the technical problems and some creative technical effects after solving the problems. Specifically:

Areas under the curve (AUCs) of performance of a deep convolutional neural network (DCNN) model based on the pelvic ultrasound image of the present disclosure for distinguishing ovarian cancer and non-cancer in an internal validation set and two external validation sets are 0.911, 0.870, and 0.831 respectively, which are superior to an average (average accuracy: internal validation set: 0.888 vs 0.857, and external validation set: 0.869 vs 0.811) of diagnosis of ovarian cancer of 35 radiologists in the internal and external validation sets. DCNN model assistance can further improve the diagnostic level of radiologists. An AUC of the DCNN for diagnosis of borderline ovarian tumors is 0.821. In the interpretation of previous pelvic ultrasound images of 12 pre-diagnosed ovarian cancer patients who had undergone multiple pelvic ultrasounds, the deep learning model successfully identified 10 potential patients with ovarian cancer 0.9 to 3.7 years earlier.

Second, considering the technical solutions as a whole or from the perspective of product, the technical effects and advantages of the technical solutions to be protected by the present disclosure are specifically described as follows:

The ultrasound image processing method for ovarian cancer provided by the present disclosure can realize automatic diagnosis of ovarian cancer by processing the ultrasound image of ovarian cancer, and has high sensitivity and specificity.

Third, as auxiliary evidence of inventiveness for the claims of the present disclosure, it is also reflected in the following important aspects:

(1) The expected income and commercial value of the technical solutions of the present disclosure after transformation are as follows:

The ultrasound image processing system will be embedded in the ultrasound equipment terminal in the future to provide a real-time auxiliary diagnosis for the radiologists, improve the working efficiency of clinicians, relieve work workload, improve the diagnostic level of radiologists in less developed regions, and make up for the defect of uneven distribution of medical resources among regions.

(2) The technical solutions of the present disclosure fill the technical gap in the industry around the world:

At present, there is no ovarian cancer diagnosis model based on deep learning and large-sample, multi-center pelvic ultrasound images. The present disclosure performs model training through images covering various pathological types of ovarian cancer acquired across equipment, regions and different ages, such that the model has strong robustness, scalability, compatibility, and universality.

(3) The technical solutions of the present disclosure solve the technical problems that people have been eager to solve but have not been successful: compared with the traditional ovarian cancer diagnosis models based on pelvic ultrasound images (such as simple rules, and adnexal), the present disclosure can realize reliable, efficient and automatic diagnosis only by relying on the ultrasound images without the reference of clinical information. Compared with other types of models for ovarian cancer diagnosis based on deep learning and pelvic ultrasound images, the present disclosure is constructed based on large-sample and multi-center pelvic ultrasound images, including images covering various pathological types of ovarian cancer acquired by different equipment in different regions at different ages, such that the model has strong robustness, scalability, compatibility, and universality.

(4) The technical solutions of the present disclosure overcome the following technical prejudice:

The present disclosure is constructed based on large-sample and multi-center pelvic ultrasound images, and includes images covering various pathological types of ovarian cancer by different equipment in different regions at different ages. The ResNet-18 model and the Darknet-19 model are used to construct the image classification model, and the model is tested by the internal and external validation sets. Therefore, the model has strong robustness, scalability, compatibility, and universality.

BRIEF DESCRIPTION OF THE DRAWINGS

To describe the technical solutions in embodiments of the present disclosure more clearly, the following briefly describes the accompanying drawings that need to be used in the embodiments. Apparently, the accompanying drawings in the following description show merely some embodiments of the present disclosure, and those of ordinary skill in the art may derive other drawings from these accompanying drawings without creative efforts.

FIG. 3A-C is a schematic diagram showing the performance of a DCNN model provided by the embodiment of the present disclosure and a radiologist in diagnosing ovarian cancer in a validation set; and FIG. 4A-B is a schematic diagram showing the performance of DCNN provided by the embodiment of the present disclosure in identifying borderline ovarian tumors.

DETAILED DESCRIPTION OF THE EMBODIMENTS

To make the objective, technical solutions and advantages of the present disclosure clearer, the present disclosure will be further described below in detail below with reference to the embodiments. Understandably, the specific embodiments described herein are merely intended to explain the present disclosure but not to limit the present disclosure.

I, Explanation of embodiment. In order to enable those skilled in the art to fully understand how the present disclosure is specifically implemented, this part is an explanatory embodiment to explain the technical solutions of the claims.

In view of the problems existing in the prior art, the present disclosure provides an ultrasound image processing method and system for ovarian cancer, a medium, a device, and a terminal. The present disclosure will be described in detail below with reference to the accompanying drawings.

Figure 1:
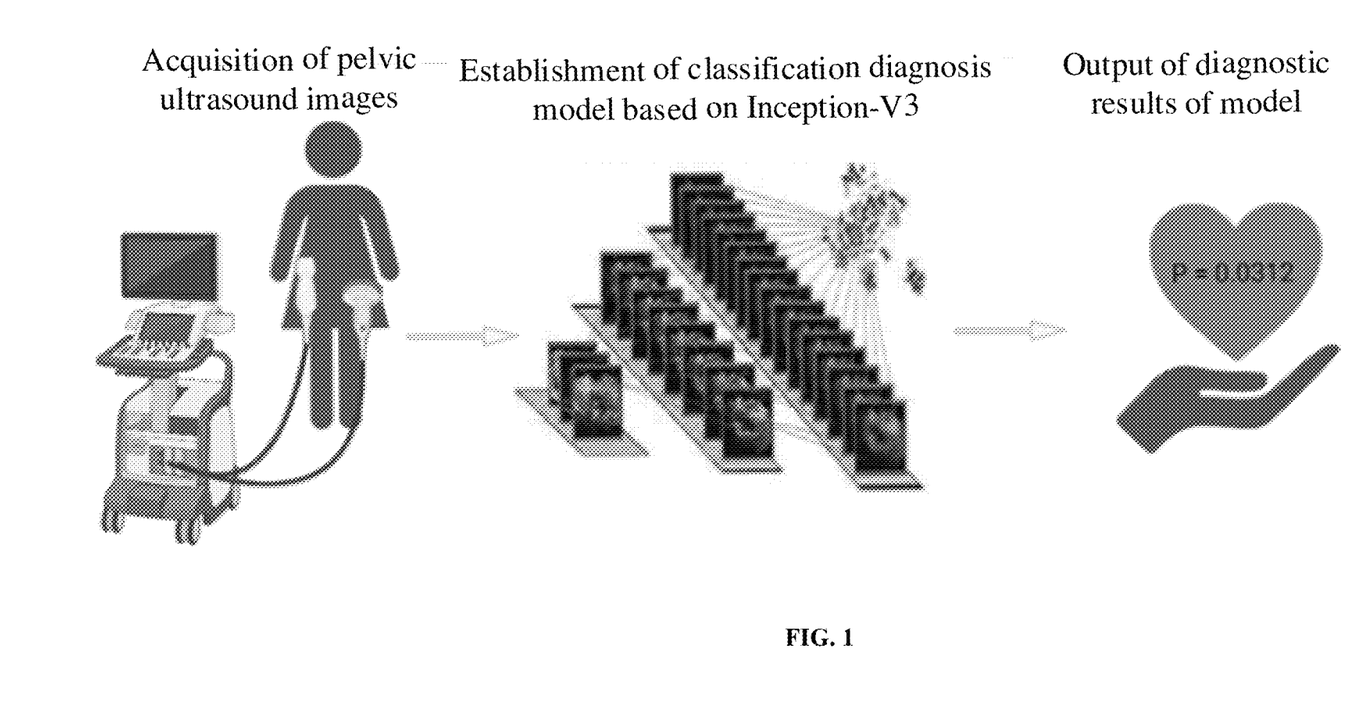
FIG. 1 is a schematic flowchart of an ultrasound image processing method for ovarian cancer provided by an embodiment of the present disclosure.

As shown in FIG. 1, an ultrasound image processing method for ovarian cancer provided by the embodiment of the present disclosure includes the following steps.

Pelvic ultrasound images and relevant clinical data of a patient are obtained.

Pelvic ultrasound image and relevant clinical information cleaning and pelvic ultrasound image quality control are performed.

An image classification model is constructed and validated.

Figure 2:
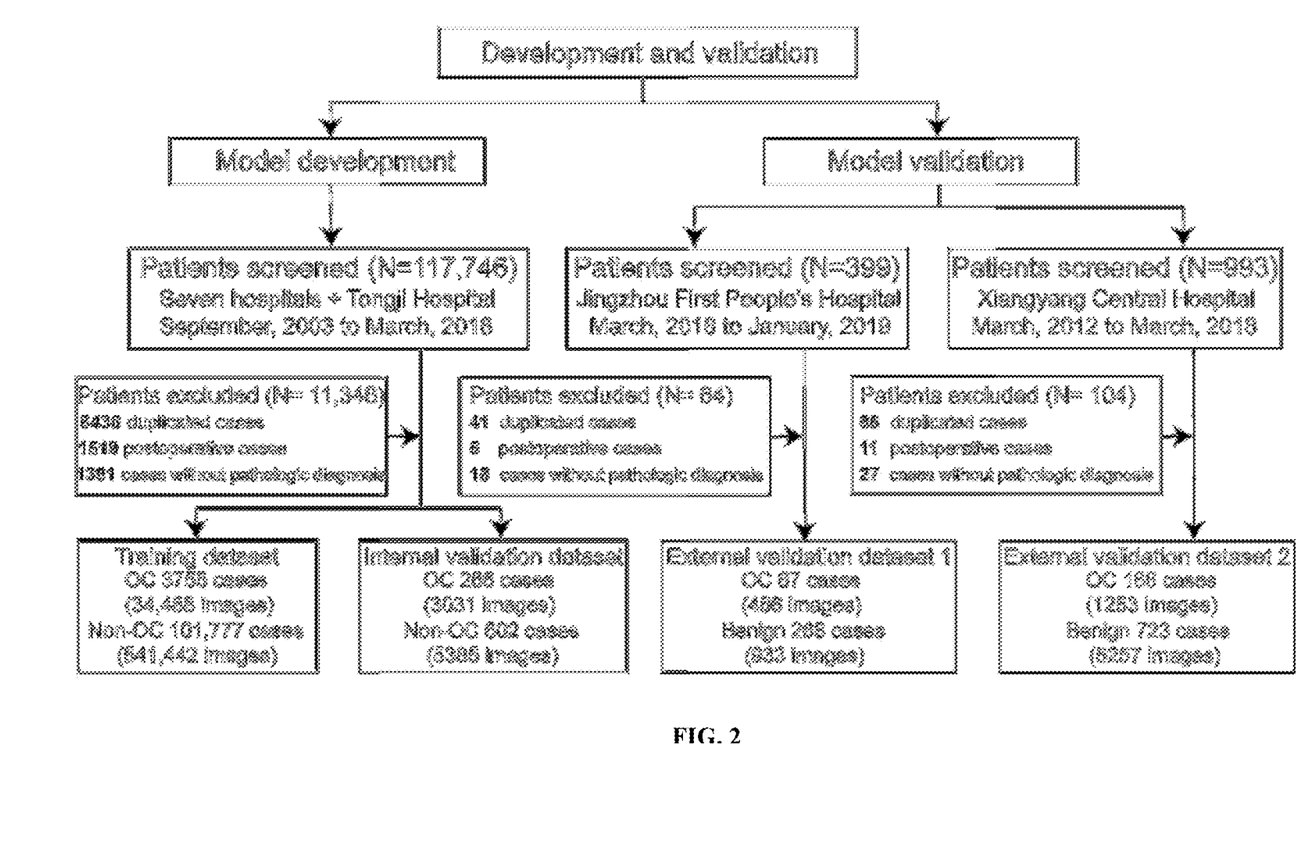
FIG. 2 is an experimental design diagram of an ultrasound image processing system for ovarian cancer provided by the embodiment of the present disclosure.

An ultrasound image processing system for ovarian cancer provided by the embodiment of the present disclosure includes: a data acquisition module, an image cleaning module, an image quality control module, and an image classification module.

The data acquisition module 1 is configured to obtain pelvic ultrasound images and relevant clinical data of a patient.

The image cleaning module 2 is configured to perform pelvic ultrasound image and relevant clinical information cleaning.

The image quality control module 3 is configured to perform pelvic ultrasound image quality control.

The image classification module 4 is configured to construct an image classification model to implement image classification.

1. Obtaining of Pelvic Ultrasound Images and Relevant Clinical Data of Patient

Information such as ultrasound images, ultrasound times, ultrasound reports (including a size and nature of a mass), patient operation times, pathological diagnosis reports (including tumor staging and grading), ages, and CA125 of a target population is retrieved through a PACS or an ultrasound workstation.

2. Pelvic Ultrasound Image Cleaning 5000 images are randomly selected from all of the pooled pelvic ultrasound images for image annotation. 10 radiologists automatically classify and mark the selected images in terms of whether the images are adnexal images, whether there are lesions, whether there are ascites, whether there are blood flow signals, whether the images are two-dimensional or three-dimensional images, and whether the images fail to be determined. Based on the above clearly marked images, an automatic image classification model for identifying whether the images are adnexal images, whether there are ascites, whether there is blood flow information, and which dimension the images belong to is constructed, so as to classify all of the images, thereby automatically eliminating ultrasound images without lesions and adnexa in batches for subsequent analysis.

3. Pelvic Ultrasound Image Quality Control

Based on 5000 images marked by 10 radiologists, a classifier automatically eliminating non-target images is constructed, and all non-adnexal images and ultrasound images of patients with benign and malignant adnexal lesions without adnexal lesion load in training set images are eliminated in batches. For example, if a pathological report of the patient shows ovarian cancer, but an image of cancer foci is incapable of being found from an anatomical position on the image, the image is eliminated.

4. Construction of Image Classification Model

A deep learning algorithm is trained using a DCNN classification model, and image input features (for example, image pixels) are mapped to corresponding output labels (for example, benign or malignant). The DCNN algorithm learns a hierarchical representation from input imaging data. This well-trained model can predict the input data. The present disclosure performs image classification using a ResNet-18 model (50 layer (ResNet-50)) and a Darknet-19 model (19 layer (Darknet-19)). Layers are functional units of neural networks, and can have different functions, since they learn and store abstract features of input images. ResNet-50 and Darknet-19 models are iteratively trained for the classification of patients with benign and malignant adnexal lesions and control images. Next, the present disclosure combines the two deep learning models by weighting their performance (measuring an AUC), and evaluates the overall DCNN model using internal and external validation sets.

The present disclosure also applies flight data enhancement to each image during training to avoid overfitting. Dynamic enhancement produces more training images through image processing, such as random cropping, rotation, horizontal or vertical flipping, scaling, translation, and adjustment of saturation and exposure, which simulates the data diversity observed in the real world, avoiding model overfitting. No image enhancement is performed on the validation set. In addition, a weight decay rate of 0.0005 is also set to further combat overfitting. Weight decay can prevent the weight of the neural network from increasing too much. To quantify the contribution of the pixels that most affect the predictions of the DCNN model, the present disclosure generates class activation maps using global average pooling in the ResNet model.

To obtain a predicted score of a single examination level, in the present disclosure, n represents a total number of images available for the patient, and Pcancer=[P1, P2, ..., Pn] represents a predicted probability of n images classified as cancer. A score θ assigned to a single examination is defined as a mean of the log-transformed Pcancer.

$$\theta = -[\ln(1-P1) + \ln(1-P2) + \ldots + \ln(1-Pn)]/n.$$

Predicted scores of the ResNet-50 and the Darknet-19 are combined and weighted by their performance.

$$\theta\text{combined} = w1 \times \theta\text{ResNet-50} + w2 \times \theta\text{Darknet-19}.$$

It is specified here:

$$w1 = \text{AUCResNet-50}/(\text{AUCResNet-50} + \text{AUCDarknet-19}), \text{ and } w2 = 1.0 - w1.$$

AUCs of performance of a DCNN model based on the pelvic ultrasound image for distinguishing ovarian cancer and non-cancer in an internal validation set and two external validation sets are 0.911, 0.870, and 0.831, respectively, which are superior to an average (average accuracy: internal validation set: 0.888 vs 0.857, and external validation set: 0.869 vs 0.811) of diagnostic performance of 35 radiologists in identifying ovarian cancer in the internal and external validation sets. DCNN model assistance can further improve the diagnostic level of radiologists. An AUC of the DCNN for diagnosis of borderline ovarian tumors is 0.821. In the interpretation of pelvic ultrasound images of 12 patients before the diagnosis of ovarian cancer who had undergone multiple pelvic ultrasounds, the deep learning model successfully identified 10 potential patients with ovarian cancer 0.9 to 3.7 years earlier.

Figure 3A:
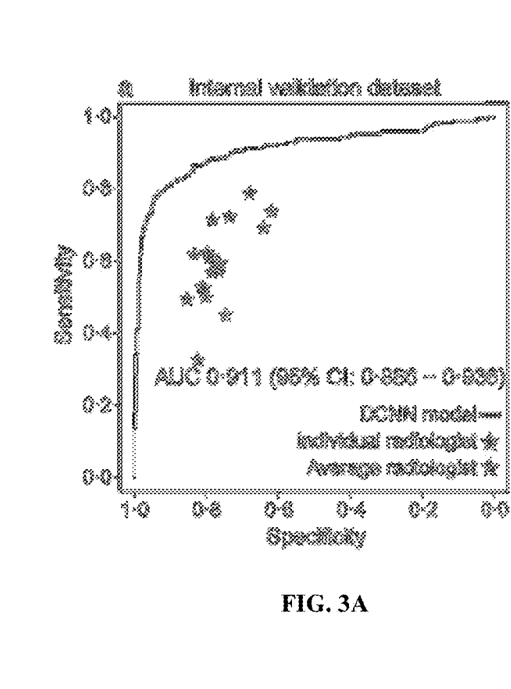
Figure 3B:
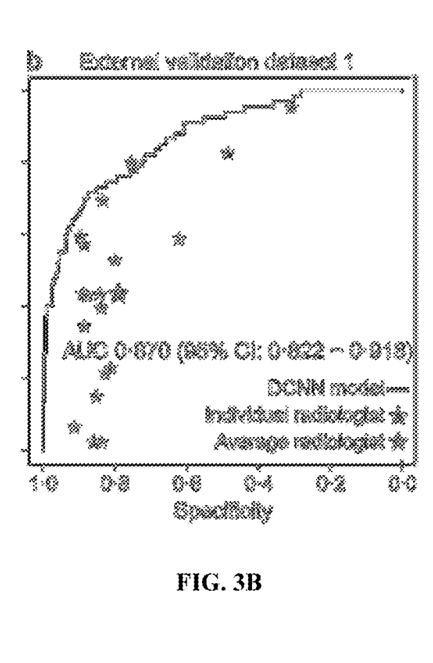
Figure 3C:
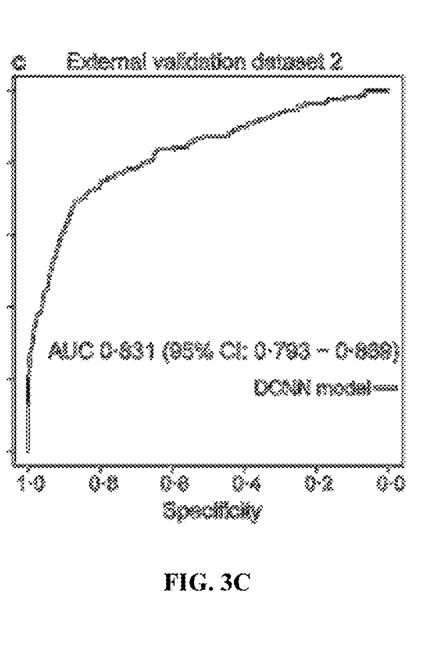
Figure 4A:
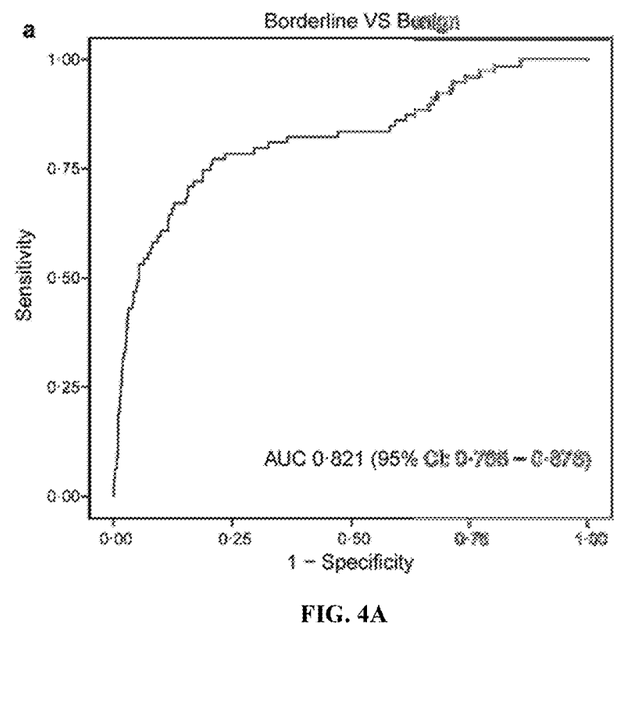
Figure 4B:
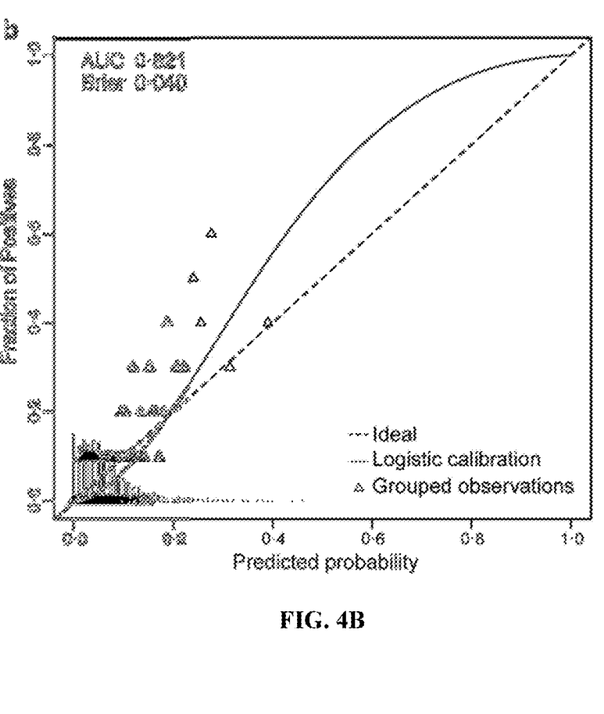

The performance of the DCNN model and the average radiologists in diagnosing ovarian cancer in the validation set is shown in FIG. 3A-C, and the performance of DCNN in identifying borderline ovarian tumors is shown in FIG. 4A-B.

TABLE 1

Performance of DCNN model and radiologist in diagnosing ovarian cancer in internal and external validation sets

|  | IVD | | EVD1 | | |
| --- | --- | --- | --- | --- | --- |
|  | Radiologists | DCNN | Radiologists | DCNN | EVD2 |
| ACC | 85.7% | 88.8% | 81.1% | 86.9% | 85.3% |
| (95% CI) | (83.4%-88.0%) | (86.5%-90.8%) | (77.8%-84.5%) | (82.8%-90.3%) | (82.8%-87.5%) |
| SN | 83.1% | 78.9% | 55.5% | 40.3% | 57.8% |
| (95% CI) | (81.4%-84.8%) | (73.5%-83.7%) | (47.3%-63.7%) | (28.5%-53.0%) | (49.9%-65.4%) |
| SP | 86.8% | 93.2% | 87.5% | 98.5% | 91.6% |
| (95% CI) | (83.6%-90.1%) | (90.9%-95.1%) | (82.3%-92.7%) | (96.2%-99.6%) | (89.3%-93.5%) |
| PPV | 74.6% | 83.7% | 58.1% | 87.1% | 61.1% |
| (95% CI) | (70.1%-79.2%) | (78.5%-88.0%) | (51.8%-64.5%) | (70.2%-96.4%) | (53.1%-68.8%) |
| NPV | 92.1% | 90.9% | 89.0% | 86.8% | 90.4% |
| (95% CI) | (91.3%-92.8%) | (88.4%-93.1%) | (87.5%-90.5%) | (82.5%-90.4%) | (88.1%-92.5%) |
| Kappa | 0.678 | 0.733 | 0.427 | 0.486 | 0.504 |
| F1 | 0.784 | 0.812 | 0.539 | 0.551 | 0.594 |

TABLE 2

Performance of 6 radiologists in diagnosing ovarian cancer before and after DCNN assistance

|  | Accuracy (95% CI) | Sensitivity (95% CI) | Specificity (95% CI) | PPV (95% CI) | NPV (95% CI) | Kappa | F1 |
| --- | --- | --- | --- | --- | --- | --- | --- |
| Radiologist A + DCNN | 0.840 (0.802-0.873) | 0.863 (0.767-0.929) | 0.835 (0.793-0.872) | 0.539 (0.449-0.628) | 0.965 (0.937-0.982) | 0.566 | 0.664 |
| Radiologist B + DCNN | 0.865 (0.830-0.896) | 0.850 (0.753-0.920) | 0.869 (0.829-0.902) | 0.591 (0.496-0.682) | 0.963 (0.936-0.981) | 0.614 | 0.697 |
| Radiologist C + DCNN | 0.902 (0.870-0.928) | 0.750 (0.641-0.840) | 0.936 (0.905-0.959) | 0.723 (0.614-0.816) | 0.944 (0.914-0.965) | 0.676 | 0.736 |
| Radiologist D + DCNN | 0.879 (0.845-0.908) | 0.838 (0.738-0.911) | 0.888 (0.851-0.919) | 0.626 (0.527-0.718) | 0.961 (0.934-0.979) | 0.642 | 0.717 |

TABLE 2-continued

Performance of 6 radiologists in diagnosing ovarian cancer before and after DCNN assistance

| | Accuracy (95% CI) | Sensitivity (95% CI) | Specificity (95% CI) | PPV (95% CI) | NPV (95% CI) | Kappa | F1 |
|---|---|---|---|---|---|---|---|
| Radiologist E + DCNN | 0.906 (0.875-0.932) | 0.825 (0.724-0.901) | 0.925 (0.892-0.950) | 0.710 (0.606-0.799) | 0.959 (0.933-0.978) | 0.705 | 0.763 |
| Radiologist F + DCNN | 0.863 (0.827-0.894) | 0.838 (0.738-0.911) | 0.869 (0.829-0.902) | 0.588 (0.492-0.679) | 0.960 (0.932-0.979) | 0.606 | 0.691 |
| Radiologist with DCNN | 0.876 (0.850-0.902) | 0.827 (0.785-0.869) | 0.887 (0.847-0.927) | 0.630 (0.553-0.706) | 0.959 (0.951-0.966) | 0.635 | 0.711 |
| Radiologist A | 0.792 (0.751-0.829) | 0.550 (0.435-0.662) | 0.846 (0.805-0.882) | 0.4444 (0.3445-0.5478) | 0.894 (0.856-0.925) | 0.363 | 0.492 |
| Radiologist B | 0.824 (0.785-0.859) | 0.688 (0.574-0.787) | 0.855 (0.814-0.890) | 0.514 (0.4154-0.6118) | 0.925 (0.891-0.951) | 0.479 | 0.588 |
| Radiologist C | 0.703 (0.658-0.746) | 0.725 (0.614-0.819) | 0.698 (0.648-0.746) | 0.3494 (0.2771-0.4271) | 0.919 (0.880-0.949) | 0.299 | 0.472 |
| Radiologist D | 0.804 (0.763-0.840) | 0.738 (0.627-0.830) | 0.818 (0.775-0.857) | 0.4758 (0.3854-0.5674) | 0.933 (0.900-0.958) | 0.458 | 0.578 |
| Radiologist E | 0.722 (0.677-0.763) | 0.875 (0.782-0.938) | 0.687 (0.636-0.735) | 0.3846 (0.3136-0.4595) | 0.961 (0.929-0.981) | 0.376 | 0.534 |
| Radiologist F | 0.854 (0.817-0.886) | 0.650 (0.535-0.753) | 0.899 (0.864-0.929) | 0.5909 (0.4809-0.6946) | 0.920 (0.887-0.946) | 0.529 | 0.619 |
| Radiologist without DCNN | 0.783 (0.721-0.845) | 0.704 (0.591-0.817) | 0.801 (0.709-0.893) | 0.460 (0.368-0.552) | 0.925 (0.902-0.948) | 0.417 | 0.547 |
| DCNN | 0.772 (0.729-0.810) | 0.875 (0.782-0.938) | 0.749 (0.700-0.793) | 0.438 (0.359-0.518) | 0.964 (0.935-0.983) | 0.449 | 0.583 |

II, Application of embodiment. In order to prove the creativity and technical value of the technical solutions of the present disclosure, this part is an application of the embodiment of the technical solutions in the claims on specific products or related technologies.

It should be noted that the embodiments of the present disclosure may be implemented by hardware, software, or a combination of software and hardware. The hardware part may be implemented using special logic. The software part may be stored in a memory and executed by a suitable instruction execution system, such as a microprocessor or specially designed hardware. Those of ordinary skill in the art will appreciate that the device and method described above may be implemented using computer-executable instructions and/or embodied in processor control code, and such a code is provided, for example, on a carrier medium such as a disk, CD or DVD-ROM, a programmable memory such as a read-only memory (firmware), or a data carrier such as an optical or electronic signal carrier. The device of the present disclosure and its modules may be implemented by hardware circuits such as very large-scale integrated circuits (VLSI) or gate arrays, semiconductors such as logic chips and transistors, or programmable hardware devices such as field programmable gate arrays and programmable logic devices, or by software executed by various types of processors, or by a combination of the above-mentioned hardware circuits and software, such as firmware.

III, Evidence of relevant effects of embodiment. The embodiments of the present disclosure have achieved some positive effects in the process of research and development or use, and indeed have great advantages compared with the prior art. The following content is described in conjunction with the data, graphs, etc. of the test process.

Compared with the traditional ovarian cancer diagnosis models based on pelvic ultrasound images (such as simple rules, and adnexal), the present disclosure can realize reliable, efficient and automatic diagnosis only by relying on the ultrasound images without the reference of clinical information. Compared with other types of models for ovarian cancer diagnosis based on deep learning and pelvic ultrasound images, the present disclosure is constructed based on large-sample and multi-center pelvic ultrasound images, including images covering various pathological types of ovarian cancer acquired by different equipment in different regions at different ages, such that the model has strong robustness, scalability, compatibility, and universality. The ultrasound image processing system will be embedded in the ultrasound equipment terminal in the future to provide real-time auxiliary diagnosis for the radiologists, improve the working efficiency of clinicians, relieve work pressure, improve the diagnostic level of radiologists in remote areas, and make up for the defect of uneven distribution of medical resources among regions.

The foregoing are merely descriptions of the specific embodiments of the present disclosure, and the protection scope of the present disclosure is not limited thereto. Any modification, equivalent replacement, improvement, etc. made within the technical scope of the present disclosure by those skilled in the art according to the spirit and principle of the present disclosure shall fall within the protection scope of the present disclosure.

What is claimed is:

1. An ultrasound image processing method for ovarian cancer identification, comprising the following steps:
   obtaining pelvic ultrasound images and relevant clinical data of a patient;
   performing pelvic ultrasound image and relevant clinical information cleaning and pelvic ultrasound image quality control;
   constructing and validating an image classification model; and
   predicating whether the patient has cancer by images available for the patient and the image classification model; wherein the constructing and validating an image classification model further comprises:
   training a deep learning algorithm using a deep convolutional neural network (DCNN) classification model, and mapping image input features to corresponding output labels, wherein the DCNN model learns a hierarchical representation from input imaging data, and the DCNN model predicts the input imaging data, and the image input features comprise image pixels, and output labels comprise benign or malignant;

performing image classification on ultrasound images using a ResNet-18 model and a Darknet-19 model to distinguish between ovarian cancer and non-cancerous cases, wherein layers are functional units of neural networks, learn and store abstract features of input images, and have different functions;

iteratively training ResNet-50 and Darknet-19 models for classification of patients with benign and malignant adnexal lesions and control images;

combining the ResNet-50 and Darknet-19 models by weighting performance and measuring an area under a curve [AUC], and evaluating the DCNN classification model using internal and external validation sets;

applying flight data enhancement to each image during training, wherein dynamic enhancement produces more training images through image processing; and setting a weight decay rate of 0.0005, and generating class activation maps using global average pooling in a ResNet model, wherein the image processing comprises random cropping, rotation, horizontal or vertical flipping, scaling, translation, and adjustment of saturation and exposure;

wherein, during predicating whether the patient has cancer by images available for the patient and the image classification model, n represents a total number of images available for the patient, and Pcancer= [P1, P2, . . . , Pn] represents a predicted probability of n images classified as cancer, so as to obtain a predicted score of a single examination level; and a score θ assigned to a single examination is defined as a mean of a log-transformed Pcancer:

$$\theta = -[\ln(1-P1) + \ln(1-P2) + \ldots + \ln(1-Pn)]/n, \text{ and}$$

predicted scores of the ResNet-50 and the Darknet-19 are combined and weighted by performance:

$$\theta \text{combined} = w1 \times \theta \text{ResNet-50} + w2 \times \theta \text{Darknet-19},$$

wherein w1=AUCResNet-50/(AUCResNet-50+AUCDarknet-19); and w2=1.0−w1.

2. The ultrasound image processing method for ovarian cancer identification according to claim 1, wherein the obtaining pelvic ultrasound images further comprises:

retrieving ultrasound images, ultrasound times, ultrasound reports, patient operation times, pathological diagnosis reports, ages, and CA125 information of a target population through a picture archiving and communication system (PACS) or an ultrasound workstation, wherein the ultrasound report comprises a size and nature of a mass, and the pathological diagnosis report comprises tumor staging and grading.

3. The ultrasound image processing method for ovarian cancer identification according to claim 1, wherein a process of performing the pelvic ultrasound image and relevant clinical information cleaning further comprises:

randomly selecting images from all of the pelvic ultrasound images for image annotation;

automatically classifying and marking, by a radiologist, the selected images in terms of whether the images are adnexal images, whether there are lesions, whether there are ascites, whether there are blood flow signals, whether the images are two-dimensional or three-dimensional images, and whether the images fail to be determined; and based on the marked images, constructing an automatic image classification model for identifying whether the images are adnexal images, whether there are ascites, whether there is blood flow information, and which dimension the images belongs to, so as to classify all of the images, thereby automatically eliminating ultrasound images without lesions and adnexa in batches for subsequent analysis.

4. The ultrasound image processing method for ovarian cancer identification according to claim 1, wherein a process of performing the pelvic ultrasound image quality control further comprises:

based on images marked by a radiologist, constructing a classifier automatically eliminating non-target images, and eliminating all non-adnexal images and ultrasound images of patients with benign and malignant adnexal lesions without adnexal lesion load in training set images in batches, wherein if a pathological report of the patient shows ovarian cancer, but an image of cancer foci is incapable of being found from an anatomical position on the image, the image is eliminated.

5. An ultrasound image processing system for ovarian cancer identification, comprising:

a data acquisition module configured to obtain pelvic ultrasound images and relevant clinical data of a patient;

an image cleaning module configured to perform pelvic ultrasound image and relevant clinical information cleaning;

an image quality control module configured to perform pelvic ultrasound image quality control; an image classification module configured to construct an image classification model to implement image classification, and predicate whether the patient has cancer by images available for the patient and the image classification model;

wherein the image classification module is further configured for:

training a deep learning algorithm using a deep convolutional neural network (DCNN) classification model, and mapping image input features to corresponding output labels, wherein the DCNN model learns a hierarchical representation from input imaging data, and the DCNN model predicts the input imaging data, and the image input features comprise image pixels, and output labels comprise benign or malignant;

performing image classification on ultrasound images using a ResNet-18 model and a Darknet-19 model to distinguish between ovarian cancer and non-cancerous cases, wherein layers are functional units of neural networks, learn and store abstract features of input images, and have different functions;

iteratively training ResNet-50 and Darknet-19 models for classification of patients with benign and malignant adnexal lesions and control images;

combining the ResNet-50 and Darknet-19 models by weighting performance and measuring an area under a curve [AUC], and evaluating the DCNN classification model using internal and external validation sets; and applying flight data enhancement to each image during training, wherein dynamic enhancement produces more training images through image processing; and setting a weight decay rate of 0.0005, and generating class activation maps using global average pooling in a ResNet model, wherein the image processing comprises random cropping, rotation, horizontal or vertical flipping, scaling, translation, and adjustment of saturation and exposure;

wherein during a process that the image classification module predicates whether the patient has cancer by images available for the patient and the image classification model, n represents a total number of images available for the patient, and Pcancer=[P1, P2, ..., Pn] represents a predicted probability of n images classified as cancer, so as to obtain a predicted score of a single examination level; and a score θ assigned to a single examination is defined as a mean of a log-transformed Pcancer:

θ=−[ln(1−$P1$)+ln(1−$P2$)+ ... +ln(1−$Pn$)]/$n$, and predicted scores of the ResNet-50 and the Darknet-19 are combined and weighted by performance:

θcombined=$w1$×θResNet-50+$w2$×θDarknet-19, wherein w1=AUCResNet-50/(AUCResNet-50+AUC-Darknet-19); and w2=1.0−w1.

6. The ultrasound image processing system according to claim 5, wherein the data acquisition module is further configured for:

retrieving ultrasound images, ultrasound times, ultrasound reports, patient operation times, pathological diagnosis reports, ages, and CA125 information of a target population through a picture archiving and communication system (PACS) or an ultrasound workstation, wherein the ultrasound report comprises a size and nature of a mass, and the pathological diagnosis report comprises tumor staging and grading.

7. The ultrasound image processing system according to claim 5, wherein the image quality control module is further configured for:

randomly selecting images from all of the pelvic ultrasound images for image annotation;

and automatically classifying and marking, by a radiologist, the selected images in terms of whether the images are adnexal images, whether there are lesions, whether there are ascites, whether there are blood flow signals, whether the images are two-dimensional or three-dimensional images, and whether the images fail to be determined; and based on the marked images, constructing an automatic image classification model for identifying whether the images are adnexal images, whether there are ascites, whether there is blood flow information, and which dimension the images belongs to, so as to classify all of the images, thereby automatically eliminating ultrasound images without lesions and adnexa in batches for subsequent analysis.

8. The ultrasound image processing system according to claim 5, wherein the image quality control module is further configured for:

based on images marked by a radiologist, constructing a classifier automatically eliminating non-target images, and eliminating all non-adnexal images and ultrasound images of patients with benign and malignant adnexal lesions without adnexal lesion load in training set images in batches, wherein if a pathological report of the patient shows ovarian cancer, but an image of cancer foci is incapable of being found from an anatomical position on the image, the image is eliminated.

9. A computer device, wherein the computer device comprises a memory and a processor, the memory stores a computer program, and when the computer program is executed by the processor, the processor implements the following steps:

obtaining pelvic ultrasound images and relevant clinical data of a patient;

performing pelvic ultrasound image and relevant clinical information cleaning and pelvic ultrasound image quality control;

constructing an image classification model to implement image classification; and predicating whether the patient has cancer by images available for the patient and the image classification model;

wherein the constructing and validating an image classification model further comprises:

training a deep learning algorithm using a deep convolutional neural network (DCNN) classification model, and mapping image input features to corresponding output labels, wherein the DCNN model learns a hierarchical representation from input imaging data, and the DCNN model predicts the input imaging data, and the image input features comprise image pixels, and output labels comprise benign or malignant;

performing image classification on ultrasound images using a ResNet-18 model and a Darknet-19 model to distinguish between ovarian cancer and non-cancerous cases, wherein layers are functional units of neural networks, learn and store abstract features of input images, and have different functions;

iteratively training ResNet-50 and Darknet-19 models for classification of patients with benign and malignant adnexal lesions and control images;

combining the ResNet-50 and Darknet-19 models by weighting performance and measuring an area under a curve [AUC], and evaluating the DCNN classification model using internal and external validation sets;

applying flight data enhancement to each image during training, wherein dynamic enhancement produces more training images through image processing; and setting a weight decay rate of 0.0005, and generating class activation maps using global average pooling in a ResNet model, wherein the image processing comprises random cropping, rotation, horizontal or vertical flipping, scaling, translation, and adjustment of saturation and exposure; and wherein, during predicating whether the patient has cancer by images available for the patient and the image classification model, n represents a total number of images available for the patient, and Pcancer=[P1, P2, ..., Pn] represents a predicted probability of n images classified as cancer, so as to obtain a predicted score of a single examination level; and a score θ assigned to a single examination is defined as a mean of a log-transformed Pcancer:

θ=−[ln(1−$P1$)+ln(1−$P2$)+ ... +ln(1−$Pn$)]/$n$, and predicted scores of the ResNet-50 and the Darknet-19 are combined and weighted by performance:

θcombined=$w1$×θResNet-50+$w2$×θDarknet-19, wherein w1=AUCResNet-50/(AUCResNet-50+AUC-Darknet-19); and w2=1.0−w1.

10. The computer device according to claim 9, wherein the obtaining pelvic ultrasound images further comprises:

retrieving ultrasound images, ultrasound times, ultrasound reports, patient operation times, pathological diagnosis reports, ages, and CA125 information of a target population through a picture archiving and communication system (PACS) or an ultrasound workstation, wherein the ultrasound report comprises a size and nature of a mass, and the pathological diagnosis report comprises tumor staging and grading.

11. The computer device according to claim 9, wherein a process of performing the pelvic ultrasound image and relevant clinical information cleaning further comprises:
randomly selecting images from all of the pelvic ultrasound images for image annotation;
automatically classifying and marking, by a radiologist, the selected images in terms of whether the images are adnexal images, whether there are lesions, whether there are ascites, whether there are blood flow signals, whether the images are two-dimensional or three-dimensional images, and whether the images fail to be determined; and based on the marked images, constructing an automatic image classification model for identifying whether the images are adnexal images, whether there are ascites, whether there is blood flow information, and which dimension the images belongs to, so as to classify all of the images, thereby automatically eliminating ultrasound images without lesions and adnexa in batches for subsequent analysis.

12. The computer device according to claim 9, wherein a process of performing the pelvic ultrasound image quality control further comprises:
based on images marked by a radiologist, constructing a classifier automatically eliminating non-target images, and eliminating all non-adnexal images and ultrasound images of patients with benign and malignant adnexal lesions without adnexal lesion load in training set images in batches, wherein if a pathological report of the patient shows ovarian cancer, but an image of cancer foci is incapable of being found from an anatomical position on the image, the image is eliminated.

* * * * *

UNITED STATES PATENT AND TRADEMARK OFFICE
CERTIFICATE OF CORRECTION

PATENT NO. : 12,394,048 B2
APPLICATION NO. : 17/935196
DATED : August 19, 2025
INVENTOR(S) : Gao et al.

It is certified that error appears in the above-identified patent and that said Letters Patent is hereby corrected as shown below:

On the Title Page

Item (73) Assignee, Please change "Tongji Hospital affiliated to Tongji Medical College of Huszhong University of Science &Technology, Wuhan (CN)" to --Tongji Hospital affiliated to Tongji Medical College of Huazhong University of Science &Technology, Wuhan (CN)--.

Signed and Sealed this
Ninth Day of December, 2025

John A. Squires
*Director of the United States Patent and Trademark Office*